(12) United States Patent
Hockenbury

(10) Patent No.: US 6,711,744 B1
(45) Date of Patent: Mar. 30, 2004

(54) SUN VISOR FOR EYEGLASSES

(76) Inventor: Rita M. Hockenbury, 13802 Menasco Ct., Houston, TX (US) 77077

( * ) Notice: Subject to any disclaimer, the term of this patent is extended or adjusted under 35 U.S.C. 154(b) by 0 days.

(21) Appl. No.: 10/096,005

(22) Filed: Mar. 13, 2002

Related U.S. Application Data

(60) Provisional application No. 60/307,659, filed on Jul. 23, 2001.

(51) Int. Cl.$^7$ .................................................. A61F 9/00
(52) U.S. Cl. .................... 2/13; 2/12; 2/209.13; 351/155
(58) Field of Search ...................... 2/10, 12, 13, 209.13, 2/175.1, 195.1, 455; 351/155

(56) References Cited

U.S. PATENT DOCUMENTS

| | | | |
|---|---|---|---|
| 2,614,255 A | * 10/1952 | Ellis | 2/12 |
| 4,262,367 A | * 4/1981 | Herrin | 2/12 |
| 4,543,667 A | * 10/1985 | Garbutt | 2/13 |
| 4,785,481 A | 11/1988 | Palmer, III et al. | |
| 4,945,573 A | * 8/1990 | Landis | 2/9 |
| D314,467 S | 2/1991 | Hall | |
| 5,005,214 A | 4/1991 | Koethe | |
| D320,609 S | 10/1991 | Cross et al. | |
| 5,113,529 A | 5/1992 | Carr | |
| D339,597 S | 9/1993 | Sprong | |
| D341,695 S | 11/1993 | Vandiver | |
| 5,826,271 A | 10/1998 | Garrett | |
| 5,933,862 A | 8/1999 | Landis | |
| 6,247,177 B1 | * 6/2001 | Hayes | 2/12 |
| 6,397,396 B1 | * 6/2002 | Vibert | 2/209.13 |

* cited by examiner

Primary Examiner—Katherine Moran
(74) Attorney, Agent, or Firm—Harrison & Egbert

(57) ABSTRACT

A sun visor device including a panel of a flexible material, a first elastic loop affixed to a bottom surface of the panel adjacent a forward edge of the panel, a second elastic loop affixed to the bottom surface of the panel adjacent a rearward edge of the panel, a third elastic loop affixed to the bottom surface of the panel adjacent to the forward edge and at an opposite end of the panel and a fourth elastic loop affixed to the bottom surface of the panel adjacent the rearward edge and adjacent to the opposite end of the panel. The panel is of a quarter moon shape. An eyeglasses frame has a first temple extending through the first and second elastic loops and a second temple extending through the third and fourth loops.

18 Claims, 3 Drawing Sheets

US 6,711,744 B1

SUN VISOR FOR EYEGLASSES

RELATED APPLICATIONS

The present application is based on and claims priority from prior filed U.S. Provisional Patent Application Ser. No. 60/307,659, filed on Jul. 23, 2001, and entitled "SUN VISOR", presently pending.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to sun visors. More particularly, the present invention relates to sun visors that are adapted to be attached to a pair of eyeglasses. More particularly, the present invention relates to sun visors which are useful in association with wire rim eyeglasses or sunglasses.

DESCRIPTION OF THE RELATED ART

In the past, various types of sun visors have been prepared so as to protect the eyes from the glare and damaging rays of the sun. Typically, these sun visors will be fastened to the head of the wearer and extend outwardly above the eyes of the wearer. Conventionally, a bill of a generally quarter moon configuration will extend outwardly from the head of the wearer a sufficient distance so as to provide shade over the wearer's eyes.

The most common type of sun visor includes a strap which extends around the head of the wearer. Often, this strap is very uncomfortable and will muss the hair of the wearer. In some circumstances, the strap will not adequately fit the size of the head of the wearer. When the wearer has on a pair of eyeglasses or sunglasses, the strap associated with the visor can often conflict with the positioning of the eyeglasses on the head of the wearer. As such, a need developed so as to allow for the use of a sun visor on or in association with the eyeglasses or sunglasses of the wearer.

Various patents, in the past, have issued relating to such eyeglass-attachable sun visors. For example, U.S. Pat. No. 4,543,667, issued on Oct. 1, 1985 to V. Garbutt describes a sun visor for attachment to a pair of eyeglass temples. The sun visor includes a bill member having a substantially flat, rigid stiffening member formed with a substantially concave inner edge and a substantially convex outer edge. A top and bottom material covers the top and bottom surfaces of the rigid stiffening member and has generally the same shape as the stiffening member. Another ribbon of material is folded over the outer edges of the bill member and the top and bottom material is secured thereto. A pair of loops of elastic material are stitched between the ribbon and the bottom material on the underside of the bill adjacent the sides where the edges meet. Unfortunately, with this type of device, the loops will tend to bend or distort wire rim glasses. There is no equalization of pressure between the respective pair of loops of elastic material. Additionally, and furthermore, the visor will tend to rest flat over the top of the eyeglasses in an uncomfortable and unattractive manner.

U.S. Pat. No. 4,785,481, issued on Nov. 22, 1988 to Palmer III et al., teaches an eye protection device which includes a frame bearing side supports. The side supports are suitable for supporting items such as goggles, eye masks and visors thereto.

U.S. Pat. No. 5,005,214, issued on Apr. 9, 1991 to T. L. Koethe, teaches an eyeglass shade visor apparatus which is removably attachable to the front frame section of a pair of eyeglasses. Support tab portions of the visor portion extend downwardly from its bottom side surface adjacent to downturned opposite ends of the visor. Each of the support tab portions has a resilient attachment loop removably secured thereto. To install the visor, the outer ends of the eyeglass temple bar members are inserted into the attachment loops.

U.S. Pat. No. 5,113,529, issued on May 19, 1992, to J. S. Carr, describes a sun visor which is adapted for attachment to the temples of eyeglasses. The sun visor is constructed of a pliable material and includes a set of slits on each side of the sun visor. The visor is secured to the temples of the eyeglasses by weaving the temples through the respective slits of each set formed in the sun visor.

U.S. Pat. No. 5,826,271, issued on Oct. 27, 1998 to L. A. Garrett, describes a sun visor which has sunglasses rotatably attached thereto so as to be movable between an up position and a down position. The sun visor is secured, by a strap, around the head of the wearer.

U.S. Pat. No. 5,933,862, issued on Aug. 10, 1999 to T. J. Landis, teaches a visor having a head band, a forwardly disposed shade and a pair of rearwardly disposed elongated support arm assemblies. The support arm assemblies are suitable for attachment to the temple portions of eyeglasses.

Various U.S. design patents have issued relating to such eyeglass-attachable visors. U.S. Pat. No. Des. 314,467, issued on Feb. 12, 1991 to R. W. Hall, shows a visor with eyeglass temples extending outwardly from a hand-shaped visor portion. U.S. Pat. No. Des. 320,609, issued on Oct. 8, 1991 to Cross et al., describes an eyeglass sun visor which has loops extending therefrom for fastening around the temples of eyeglasses. U.S. Pat. No. Des. 339,597, issued on Sep. 21, 1993 to T. Sprong, shows a visor formed of a suitable material with button assemblies at opposite ends for securing around the temples of eyeglasses. U.S. Pat. No. Des. 341,695, issued on Nov. 30, 1993 to K. A. Vandiver, shows a visor which includes a slit thereon suitable for allowing the temples of eyeglasses to pass therethrough.

The problem with these prior art device is their inability to be used with wire rim eyeglasses. Uneven pressures applied to such wire rims will distort or damage the actual wire frame of the glasses. Furthermore, when they are placed upon wire rim eyeglasses, these prior art sun visors often reside loosely and unattractively directly onto the top of the frame of the eyeglasses. These visors are often loosely connected to the rims of the glasses so that they slide back and forth and flop up and down. In other circumstances, the back edge of such sun visors will fit tightly against the forehead of the wearer so as to muss the hair of the wearer or leave unattractive visor marks on the skin of the wearer.

It is an object of the present invention to provide a sun visor which is suitable for attachment to wire rim eyeglasses and/or sunglasses.

It is another object of the present invention to provide a sun visor which can be secured in an arcuate shape above the top of the frame of the eyeglasses.

It is another object of the present invention to provide a sun visor which avoids the mussing of the wearer's hair or the marking of the wearer's skin.

It is another object of the present invention to provide a sun visor that fits securely upon wire rim glasses.

It is a further object of the present invention to provide a sun visor that includes a shape whereby a hem can be easily affixed thereover.

It is still another object of the present invention to provide a sun visor which is easy to install, easy to manufacture and relatively inexpensive.

These and other objects and advantages of the present invention will become apparent from a reading of the attached specification.

SUMMARY OF THE INVENTION

The present invention is a sun visor which is suitable for attachment to a pair of sunglasses or eyeglasses. As used herein, the term "eyeglasses" will encompass such sunglasses, spectacles and related items.

The sun visor of the present invention includes a panel in the shape of a bill formed of a flexible material and in a quarter-moon shape. The flexible material can be a variety of materials which are commonly used for the bills of caps. For example, the flexible material can be cloth over cardboard, a plastic material, a fibrous material, or similar material. The panel has a forward edge, a rearward edge and side corners formed at the ends of the panel between the forward edge and the rearward edge. The panel also has a top surface and a bottom surface.

A first elastic loop is affixed to the bottom surface of the panel adjacent to the forward edge at one corner. The first elastic loop extends toward the rearward edge for less than one-half of the width of the visor in that area. A second elastic loop is affixed to the panel on the bottom surface adjacent to the rearward edge at such corner. The second elastic loop will extend toward the forward edge and will extend for less than one-half of the width of the visor at that location. The first and second elastic loops are suitable for receiving the temple of eyeglasses therein.

A third elastic loop and a fourth elastic loop are formed at the opposite corner of the panel in the same orientation as the first elastic loop and the second elastic loop. The opposite temple of the eyeglasses are received by the third elastic loop and the fourth elastic loop. When the elastic loops are secured around the respective temples of the eyeglasses, the bottom surface of the panel will have an arcuate shape extending above the top of the rim of the eyeglasses. The rearward edge of the panel will be suitably spaced from the forehead of the wearer.

The forward edge and the rearward edge of the panel converge at opposite ends of the panel. The first and second elastic loops are affixed inwardly of one end of the panel. Similarly, the third and fourth elastic loops are positioned inwardly of the opposite end of the panel. A hem is affixed around the periphery of the panel along the forward edge and the rearward edge. The hem along the forward edge of the panel has its end connected to the hem along the rearward edge of the panel. Each of the first, second, third and fourth elastic loops are affixed so as to be interposed between the respective hem and the panel.

DETAILED DESCRIPTION OF THE INVENTION

Figure 1:
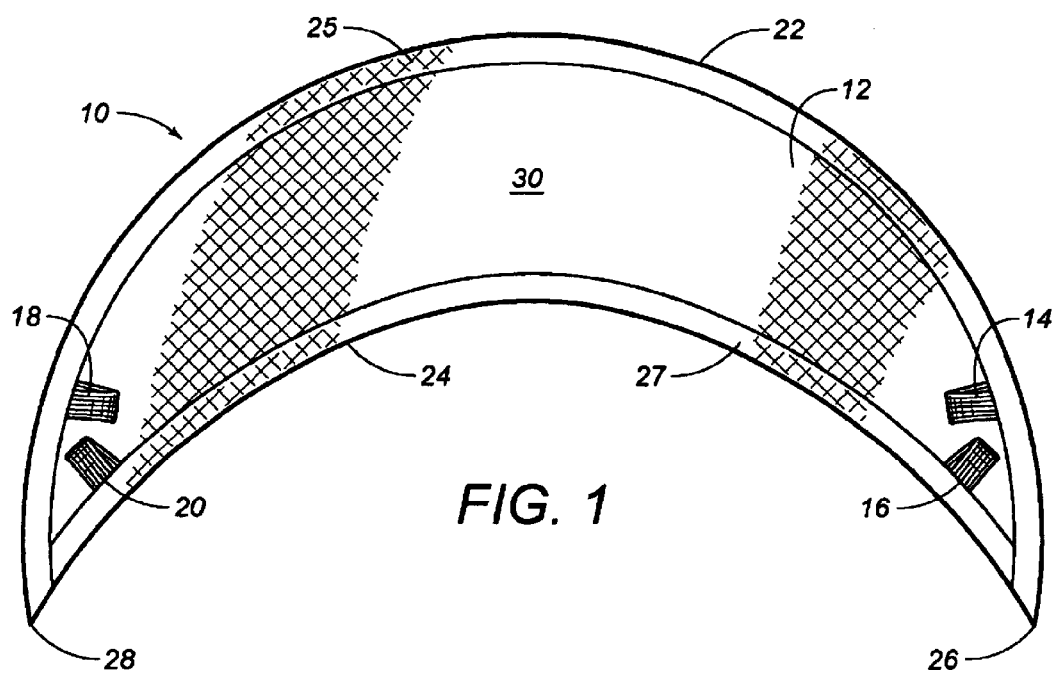
FIG. 1 is a bottom view of the sun visor of the present invention.

Referring to FIG. 1, there is shown at 10 the sun visor in accordance with the teachings of the present invention. The sun visor 10 includes a panel 12 having a first elastic loop 14, a second elastic loop 16, a third elastic loop 18 and a fourth elastic loop 20 secured thereto. The panel 12 has a forward edge 22 and a rearward edge 24. The forward edge 22 and the rearward edge 24 converge at corners 26 and 28 at the opposite sides of the panel 12. The bottom surface 30 of the sun visor 10 is shown in FIG. 1.

The panel 12 is formed of a flexible material such as a cardboard material, a fiberboard material, a cloth-over-cardboard material, a plastic material or similar semi-rigid construction. The panel 12 has a quarter-moon shape. The forward edge 22 is convex and the rearward edge 24 is concave. In the preferred form of the present invention, a hem 25 will extend around the forward edge 22 of the panel 12. Similarly, another hem 27 will extend around the rearward edge 24 of the panel 12. Each of the elastic loops 14 and 18 are interposed between the inner surface of the hem 25 and the bottom surface 30 of the panel 12. Similarly, the elastic loops 16 and 20 are interposed between the hem 27 and the panel 30. The hems 25 and 27 present a more attractive appearance for the sun visor 10 of the present invention. The securing of the elastic loops 14, 16, 18 and 20, between the panel 12 and the respective hems, enhances the securement of such loops to the sun visor 10. Additionally, and importantly, it was found that the converging corners 26 and 28 should be slightly pointed so that the securement of the hems 25 and 27 is easy. If the corners 26 and 28 were rounded or squared, then it was found that the application of the hems 25 and 27 could become bunched in such areas. The pointed corners 26 and 28 enhance the attractiveness of the sun visors and also enhance the ability to install the hems 25 and 27.

The first elastic loop 14 is affixed to the panel 12 adjacent to the forward edge 22 and adjacent to corner 26. The first elastic loop 14 will extend inwardly from the forward edge 22 for less than half of the width of the panel 12 in the area of the loop 14. The elastic loop 14 can be sewn or adhesively secured adjacent to the forward edge 22. A second elastic loop 16 is affixed to the panel 12 adjacent to the rearward edge 24 at the corner 26. The second elastic loop 16 is closer to the corner 26 than is the first elastic loop 14. The second elastic loop 16 will similarly extend for less than one half of the width of the panel 12 in the area of the loop 16. The first elastic loop 14 and the second elastic loop 16 are suitably positioned and suitably elastic so as to allow for the temple of the eyeglasses to be received therein. The temple can simply be attached by threading the temple through the first elastic loop 14 and then threading the same temple through the second elastic loop 16 until the temple extends outwardly of the corner 26.

The third elastic loop 18 is affixed to the panel 12 adjacent to the forward edge 22 at the corner 28. The third elastic loop 18 will similarly extend for less than half of the width of the panel 12 in the area of loop 18. The third elastic loop 18 will extend toward the rearward edge 24. The fourth elastic loop 20 is affixed adjacent to the rearward edge 24 of the panel 12 and extends toward the forward edge 22. The fourth elastic loop 20 is closer to the corner 28 than is the third elastic loop 18. The fourth elastic loop 20 will similarly extend for less than half of the width of the visor in the area of loop 20. The opposite temple of the eyeglasses can be installed in the third elastic loop 18 and the fourth elastic loop 20 in the same manner as was described hereinbefore. The elastic loops 18 and 20 will suitably expand so as to receive the temple therein.

It is important to note that the elastic loops 14, 16, 18 and 20 are suitably expandable so as to exert a small pressure on the respective temples of the eyeglasses. However, since this pressure is coming from opposite sides of the respective temples (by the placement of the elastic loops on either the forward edge 22 or the rearward edge 24), damage to the wire rim temples is effectively avoided. Unlike the prior art, this opposite placement of elastic loops avoids distortion or bending of the fragile wire rim eyeglasses. This particular placement of the respective loops 14, 16, 18 and 20 will also assure that the panel 12 will assume an arcuate shape extending above and spaced from the top edge of the rim of the eyeglasses while also being spaced outwardly from the forehead of the wearer.

Figure 2:
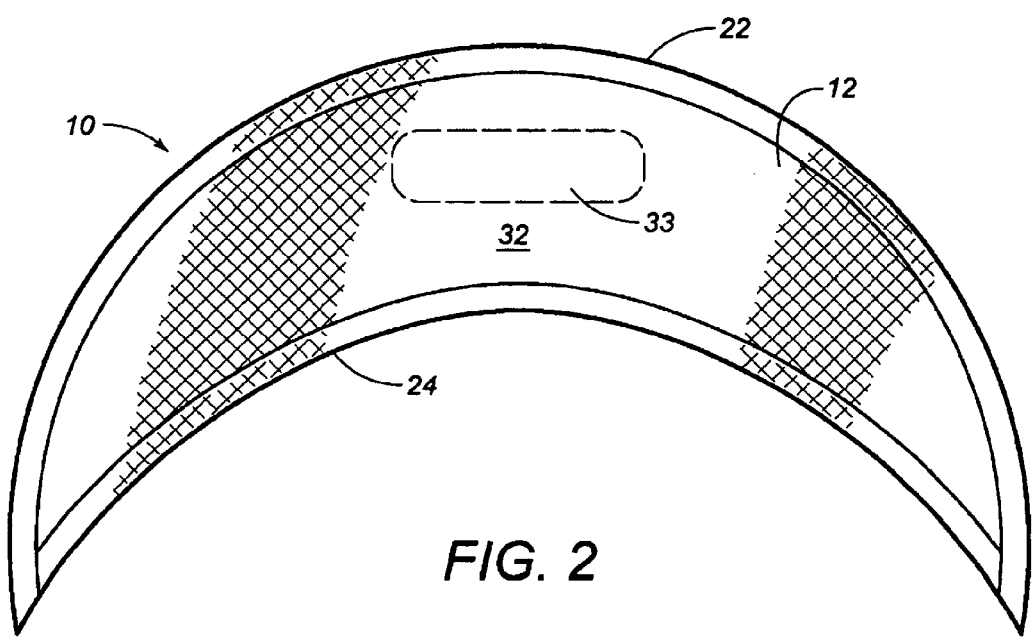
FIG. 2 is a top view of the sun visor of the present invention.

FIG. 2 shows the top surface 32 of the panel 12 of the sun visor 10. The panel 12 will generally have a planar construction prior to installation on the eyeglasses. The top surface 32 can have a suitable area 33 for the placement of decoration and/or advertising indicia.

Figure 3:
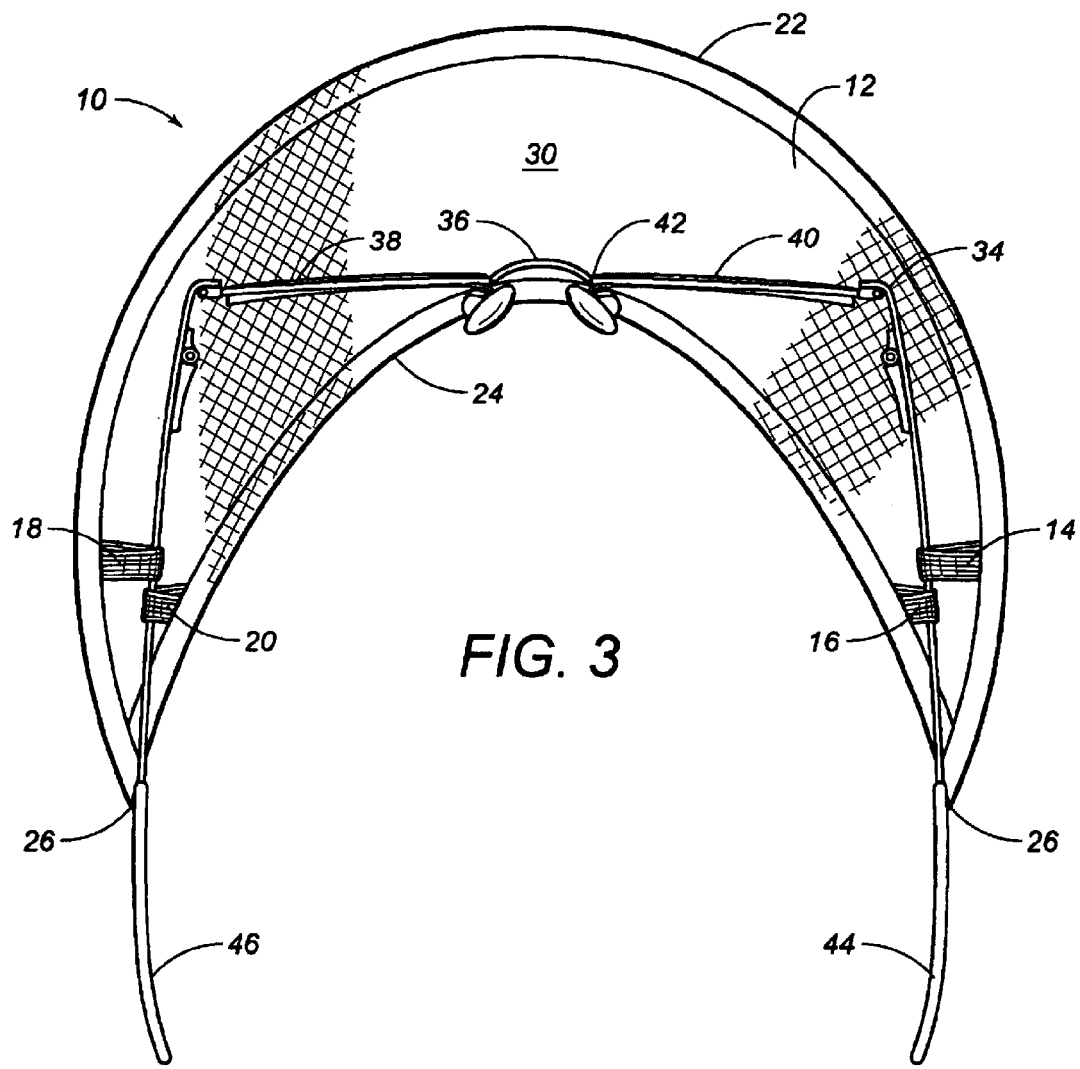
FIG. 3 is a bottom view showing the attachment of the sun visor of the present invention to a pair of eyeglasses.

FIG. 3 shows the manner of attachment of the eyeglasses 34 to the sun visor 10. The eyeglasses 34 includes a frame 36 suitable for receiving lenses 38 and 40 therein. The frame 36 has a top edge 42 which will be spaced from the bottom surface 30 of the panel 12 of the sun visor 10. The eyeglasses 34 also have temples 44 and 46 extending from the frame 36. In the preferred embodiment of the present, invention, the frame 36 and the temples 44 and 46 will be of a wire-like construction.

It can be seen that the first temple 44 is received by the first elastic loop 14 and the second elastic loop 16. Since the elastic loops 14 and 16 are in close proximity to each other, the pressure applied to the wire material of the temple 44 is counterbalanced so as to avoid deformation or bending of the temple 44. Similarly, the temple 46 is received within the third elastic loop 18 and the fourth elastic loop 20. In this manner, the visor 10 is securely placed upon the eyeglasses 34.

Figure 4:
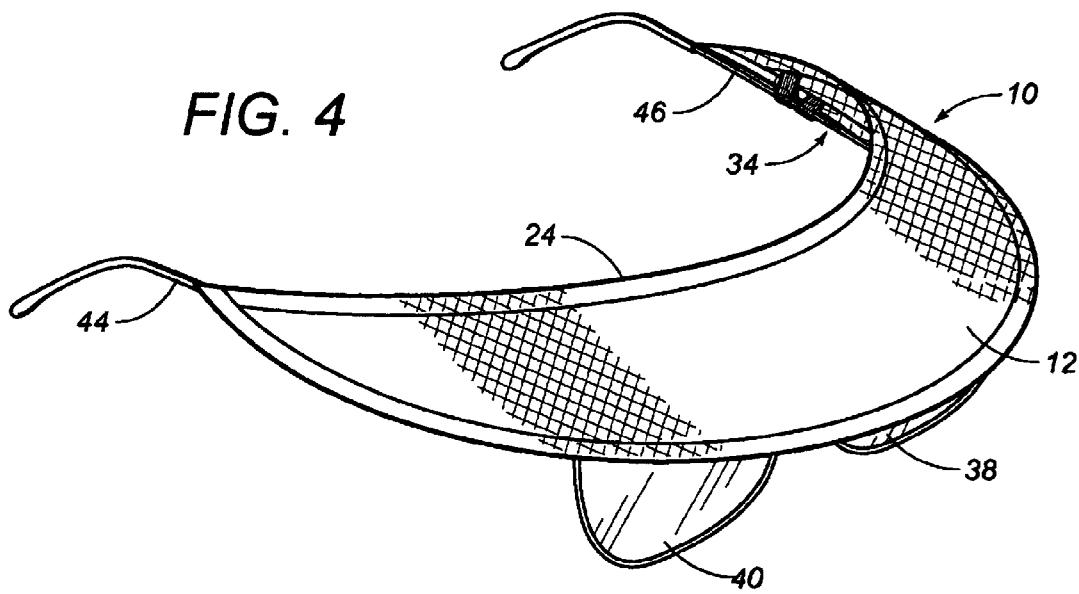
FIG. 4 is an upper perspective showing the placement of the sun visor of the present invention upon the wire rim eyeglasses.

FIG. 4 shows the manner in which the visor 10 resides above the lenses 38 and 40 of the eyeglasses 34. The panel 12 of the sun visor 10 will assume a rather curved or arcuate configuration above the top of the lenses 38 and 40. The sun visor 10 extends outwardly a sufficient distance from the lenses 38 and 40 so as to provide adequate sun shielding capability. The arcuate shape of the sun visor 10 will avoid any hair mussing or skin marking caused by the rearward edge 24. Temples 44 and 46 extend outwardly beyond the rearward edge 24 of the panel 12.

Figure 5:
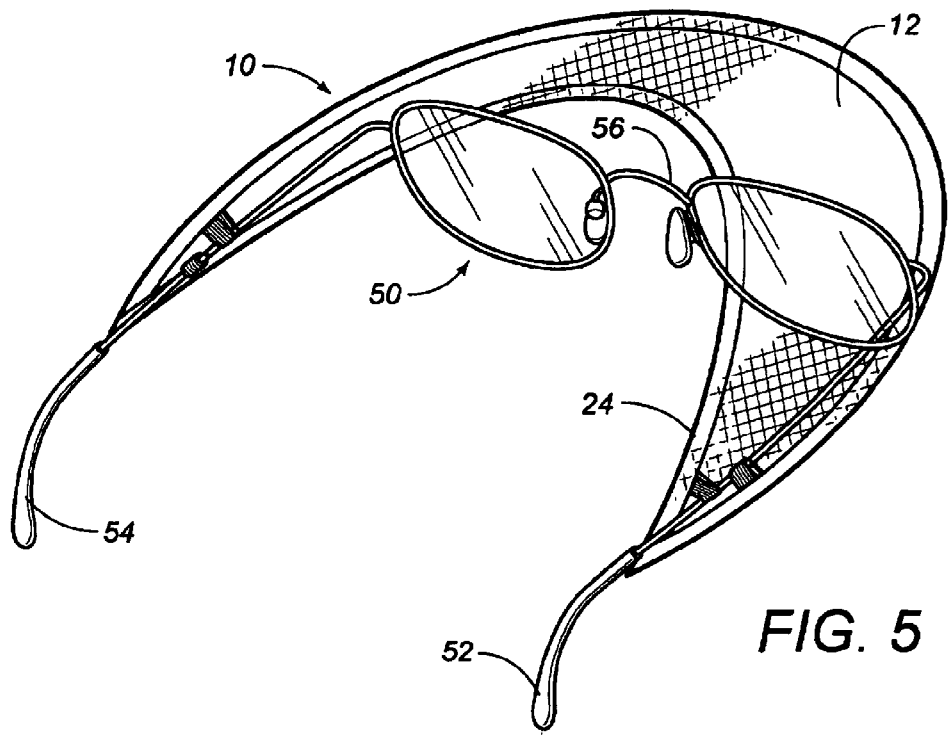
FIG. 5 is a bottom perspective showing the securing of the sun visor to a conventional pair of eyeglasses using a conventional frame.

FIG. 5 also shows the sun visor 10 as applied to a different set of eyeglasses 50. Eyeglasses 50 can be of a rigid frame construction, such as horn rim eyeglasses. The respective elastic loops on the panel 12 of the sun visor 10 can be placed around the temples 52 and 54 of eyeglasses 50 in the same manner as with wire rim glasses. In FIG. 5, it can be seen that the rearward edge 24 extends above the top of the frame 56 in a curved manner. The specific positioning of the elastic loops 14, 16, 18 and 20 will, surprisingly, assure that the panel 12 of the sun visor 10 takes on this arcuate shape. This arcuate shape enhances the appearance of the sun visor 10 and adds strength and rigidity to the sun visor 10.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

I claim:

1. A sun visor device comprising:
    a panel of flexible material, said panel having a forward edge and a rearward edge, said panel having a top surface and a bottom surface;
    a first elastic loop affixed to said bottom surface of said panel adjacent said forward edge and adjacent one end of said panel;
    a second elastic loop affixed to said bottom surface of said panel adjacent said rearward edge and adjacent said one end of said panel;
    a third elastic loop affixed to said bottom surface of said panel adjacent said forward edge and adjacent an opposite end of said panel; and
    a fourth elastic loop affixed to a bottom surface of said panel adjacent said rearward edge and adjacent said opposite end of said panel, said first elastic loop extending toward said rearward edge for less than one-half of a width of said panel at said first elastic loop, said second elastic loop extending toward said forward edge for less than one-half of a width of said panel at said second elastic loop.

2. The device of claim 1, said forward edge and said rearward edge converging at said one end of said panel and at said opposite end of said panel.

3. The device of claim 2, said first and second elastic loops positioned inwardly of said one end of said panel, said third and fourth elastic loops positioned inwardly at said opposite end of said panel.

4. The device of claim 1, said panel being of a quarter moon shape.

5. The device of claim 1, said panel having a hem of a cloth material affixed thereover along said forward and rearward edges.

6. The device of claim 5, each of said first elastic loop, said second elastic loop, said third elastic loop and said fourth elastic loop having a portion interposed between said hem and said panel.

7. The device of claim 1, said third elastic loop extending toward said rearward edge for less than one-half of a width of said panel at said third elastic loop, said fourth elastic loop extending toward said forward edge for less than one-half of a width of said panel at said fourth elastic loop.

8. The device of claim 1, said third and fourth elastic loops having a similar orientation respectively on said bottom surface as said first and second elastic loops.

9. The device of claim 1, said top surface of said panel having display indicia printed thereon.

10. The device of claim 1, further comprising:
    an eyeglasses frame having a first temple extending outwardly from one side thereof and a second temple extending outwardly from an opposite side thereof, said first and second elastic loops receiving said first temple therethrough, said third and fourth elastic loops receiving said second temple therethrough.

11. The device of claim 10, said panel extending in an arcuate shape above said eyeglasses frame.

12. An apparatus comprising:
    an eyeglasses frame with a first temple extending outwardly from one side thereof and a second temple extending outwardly from an opposite side thereof;

a panel having a forward edge and a rearward edge, said panel having a top surface and a bottom surface;

a first elastic loop adjacent said forward edge of said panel;

a second elastic loop adjacent said rearward edge of said panel, said first temple extending through said first and second elastic loops;

a third elastic loop affixed adjacent said forward edge of said panel; and a fourth elastic loop affixed adjacent said rearward edge of said panel, said second temple extending through said third and fourth elastic loops, said first elastic loop extending toward said rearward edge for less than one-half of the width of said panel at said first elastic loop, said second elastic loop extending toward said forward edge for less than one-half of the width of said panel at said second elastic loop.

13. The apparatus of claim 12, said forward edge and said rearward edge converging at an opposite end of said panel, said first and second elastic loops positioned adjacent said one end of said panel, said third and fourth elastic loops positioned adjacent said opposite end of said panel.

14. The apparatus of claim 12, said panel being of a flexible material and having a quarter moon shape.

15. The apparatus of claim 12, said third elastic loop extending toward rearward edge for less than one-half of the width of said panel at said third elastic loop, said fourth elastic loop extending toward said forward edge for less than one-half of the width of the panel at said fourth elastic loop.

16. The apparatus of claim 12, said third and fourth elastic loops having a similar orientation respectively on said bottom surface of said panel as said first and second elastic loops.

17. The apparatus of claim 12, said panel having an arcuate shape curving upwardly above a top of said eyeglasses frame.

18. The apparatus of claim 12, said panel having a hem of cloth material affixed thereover along said forward and rearward edges, each of said first elastic loop and said second elastic loop and said third elastic loop and said fourth elastic loop having a portion interposed between said hem and said panel.

* * * * *